US011692720B2

(12) United States Patent
Shaffer et al.

(10) Patent No.: US 11,692,720 B2
(45) Date of Patent: Jul. 4, 2023

(54) AIR CONDITIONER UNIT HAVING A STERILIZATION LIGHT ASSEMBLY

(71) Applicant: Haier US Appliance Solutions, Inc., Wilmington, DE (US)

(72) Inventors: Timothy Scott Shaffer, La Grange, KY (US); Craig Benjamin Williams, Louisville, KY (US); Stephen Budelsky, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 80 days.

(21) Appl. No.: 17/306,093

(22) Filed: May 3, 2021

(65) Prior Publication Data

US 2022/0349590 A1 Nov. 3, 2022

(51) Int. Cl.
*F24F 1/0328* (2019.01)
*A61L 9/20* (2006.01)
*F24F 8/22* (2021.01)

(52) U.S. Cl.
CPC .............. *F24F 1/0328* (2019.02); *A61L 9/20* (2013.01); *F24F 8/22* (2021.01); *A61L 2209/16* (2013.01)

(58) Field of Classification Search
CPC .......... F24F 1/0328; F24F 8/22; F24F 1/0071; A61L 9/20; A61L 2209/16
USPC .......................................................... 62/264
See application file for complete search history.

(56) References Cited

U.S. PATENT DOCUMENTS

| 7,251,953 | B2 | 8/2007 | Wetzel | |
|---|---|---|---|---|
| 10,088,175 | B2 | 10/2018 | Joung | |
| 2005/0163652 | A1 | 7/2005 | Crawford | |
| 2006/0021375 | A1* | 2/2006 | Wetzel | F24F 3/167 62/419 |
| 2011/0011112 | A1* | 1/2011 | Goel | F24F 8/22 29/890.03 |
| 2017/0198934 | A1* | 7/2017 | Shaffer | F24F 11/30 |
| 2019/0093906 | A1 | 3/2019 | Volle | |

* cited by examiner

*Primary Examiner* — Steve S Tanenbaum
(74) *Attorney, Agent, or Firm* — Dority & Manning, P.A.

(57) ABSTRACT

An air conditioner unit may include a housing, an outdoor heat exchanger assembly, an indoor heat exchanger assembly, a compressor, a bulkhead, and a sterilization light assembly. The housing may define an indoor portion and an outdoor portion. The housing may further define an exhaust outlet downstream from the indoor portion to exhaust air. The outdoor heat exchanger assembly may be disposed in the outdoor portion and include an outdoor heat exchanger. The indoor heat exchanger assembly may be disposed in the indoor portion and include an indoor heat exchanger and an indoor fan. The bulkhead may be disposed between the outdoor heat exchanger and the indoor heat exchanger along a transverse direction to define the indoor portion and the outdoor portion. The bulkhead may further define a vent aperture therethrough. The sterilization light assembly may be disposed within the indoor portion downstream from the vent aperture.

20 Claims, 8 Drawing Sheets

FIG. 8

AIR CONDITIONER UNIT HAVING A STERILIZATION LIGHT ASSEMBLY

FIELD OF THE INVENTION

The present subject matter relates generally to air conditioner units and more particularly to an air conditioner unit having a sterilization light assembly for sterilizing air within the air conditioner unit.

BACKGROUND OF THE INVENTION

Air conditioner or conditioning units are conventionally used to adjust the temperature indoors (i.e., within structures such as dwellings and office buildings). For example, a packaged terminal air conditioners (PTAC) may be used to adjust the temperature in, for example, a single room or group of rooms of a structure. A PTAC unit includes an indoor portion and an outdoor portion. The indoor portion generally communicates (e.g., exchanges air) with the room/group of rooms within a building, and the outdoor portion generally communicates (e.g., exchanges air) with the area outside the building. Accordingly, the air conditioner unit generally extends through, for example, a wall of the structure. Generally, a fan may be operable to rotate to motivate air through the indoor portion. Another fan may be operable to rotate to motivate air through the outdoor portion. A sealed cooling system including a compressor is generally housed within the air conditioner unit to treat (e.g., cool or heat) air as it is circulated through, for example, the indoor portion of the air conditioner unit.

One issue that may arise during the use of a conventional air conditioner unit (e.g., PTAC) is the presence of potentially damaging microbes, bacteria, or viruses within the surrounding air. In particular, the such microbes, bacteria, or viruses may be circulated or propelled through a room as an air conditioner unit draws in and expels air. The issue may be magnified if makeup is required to mix outdoor air with indoor air. This may, in turn, make it difficult to prevent transmission of such microbes, bacteria, or viruses to individuals located within the same room. Although some attempts have been made to use the sterilization properties of ultraviolet (UV) light to help reduce or eliminate microbes, bacteria, or viruses; these attempts may have a number of drawbacks. For instance, it can be difficult to direct light to a significant portion of air flowing through an air conditioner unit without requiring a light assembly that is especially bulky or energy intensive. Additionally or alternatively, it may be difficult to mount a light assembly in such a way that it can reliably sterilize air while preventing damage that might occur to the light assembly (e.g., from moisture or excessive heat generated within an air conditioner unit).

As a result, an air conditioner unit addressing one or more of the above issues would be useful. In particular, it may be advantageous to provide an air conditioner unit having features for effectively or reliably sterilizing air flowing therethrough (e.g., without significant increases to system size, cost to manufacture or operate, etc.).

BRIEF DESCRIPTION OF THE INVENTION

Aspects and advantages of the invention will be set forth in part in the following description, or may be obvious from the description, or may be learned through practice of the invention.

In one exemplary aspect of the present disclosure, an air conditioner unit is provided. The air conditioner unit may include a housing, an outdoor heat exchanger assembly, an indoor heat exchanger assembly, a compressor, a bulkhead, and a sterilization light assembly. The housing may define an indoor portion and an outdoor portion. The housing may further define an exhaust outlet downstream from the indoor portion to exhaust air therefrom. The outdoor heat exchanger assembly may be disposed in the outdoor portion and include an outdoor heat exchanger. The indoor heat exchanger assembly may be disposed in the indoor portion and include an indoor heat exchanger and an indoor fan. The compressor may be in fluid communication with the outdoor heat exchanger and the indoor heat exchanger to circulate a refrigerant between the outdoor heat exchanger and the indoor heat exchanger. The bulkhead may be disposed between the outdoor heat exchanger and the indoor heat exchanger along a transverse direction. The bulkhead may define the indoor portion and the outdoor portion. The bulkhead may further define a vent aperture therethrough. The sterilization light assembly may be disposed within the indoor portion downstream from the vent aperture.

In another exemplary aspect of the present disclosure, an air conditioner unit is provided. The air conditioner unit may include a housing, an outdoor heat exchanger assembly, an indoor heat exchanger assembly, a compressor, a bulkhead, and a sterilization light assembly. The housing may define an indoor portion and an outdoor portion. The housing may further define an exhaust outlet downstream from the indoor portion to exhaust air therefrom. The outdoor heat exchanger assembly may be disposed in the outdoor portion and include an outdoor heat exchanger. The indoor heat exchanger assembly may be disposed in the indoor portion and include an indoor heat exchanger and an indoor fan. The compressor may be in fluid communication with the outdoor heat exchanger and the indoor heat exchanger to circulate a refrigerant between the outdoor heat exchanger and the indoor heat exchanger. The bulkhead may be disposed between the outdoor heat exchanger and the indoor heat exchanger along a transverse direction. The bulkhead may define the indoor portion and the outdoor portion. The bulkhead may further define a vent aperture therethrough. The sterilization light assembly may be disposed within the indoor portion downstream from the vent aperture and below the indoor fan. The sterilization light assembly may be directed at the vent aperture to sterilize makeup air therefrom.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the term "or" is generally intended to be inclusive (i.e., "A or B" is intended to mean "A or B or both"). The terms "first," "second," and "third" may be used interchangeably to distinguish one component from another and are not intended to signify location or importance of the individual components. The terms "upstream" and "downstream" refer to the relative flow direction with respect to fluid flow (e.g., airflow or refrigerant flow) in a fluid pathway. For example, "upstream" refers to the flow direction from which the fluid flows, and "downstream" refers to the flow direction to which the fluid flows.

Figure 1:
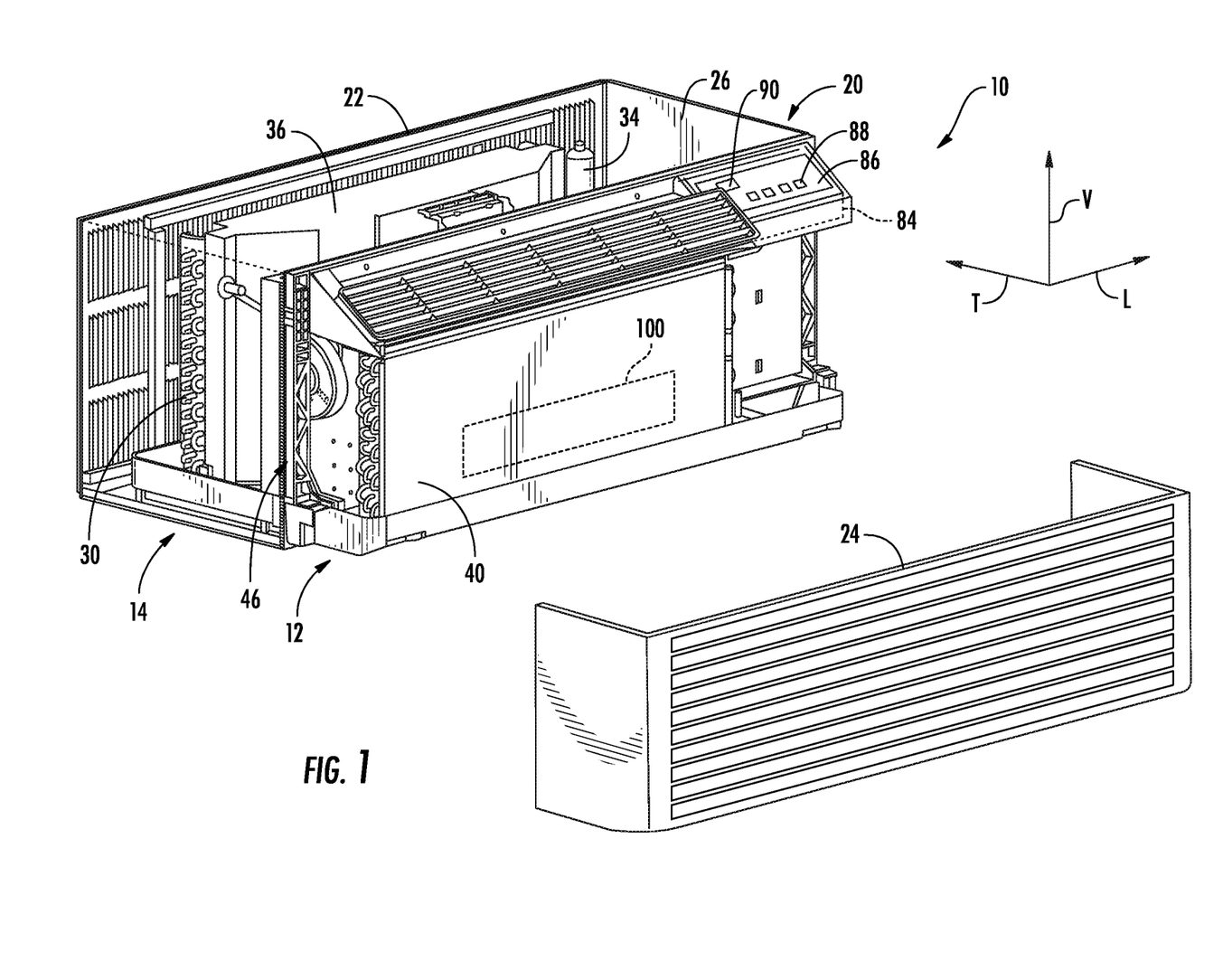
FIG. 1 provides a perspective view of an air conditioner unit, with part of an indoor portion exploded from a remainder of the air conditioner unit for illustrative purposes, according to exemplary embodiments of the present disclosure.

Referring now to FIG. 1, an air conditioner unit 10 is provided. The air conditioner unit 10 is a one-unit type air conditioner, also conventionally referred to as a packaged terminal air conditioner (PTAC) unit. The unit 10 includes an indoor portion 12 and an outdoor portion 14, and generally defines a vertical direction V, a lateral direction L, and a transverse direction T. Each direction V, L, T is perpendicular to each other, such that an orthogonal coordinate system is generally defined.

A housing 20 of the unit 10 may contain various other components of the unit 10. Housing 20 may include, for example, a rear grill 22 and a room front 24 which may be spaced apart along the transverse direction T by a wall sleeve 26. The rear grill 22 may be part of the outdoor portion 14, and the room front 24 may be part of the indoor portion 12. Components of the outdoor portion 14, such as an outdoor heat exchanger 30, outdoor fan 32, and compressor 34 may be housed within the wall sleeve 26. A casing 36 may additionally enclose the outdoor fan 32, as shown.

Figure 2:
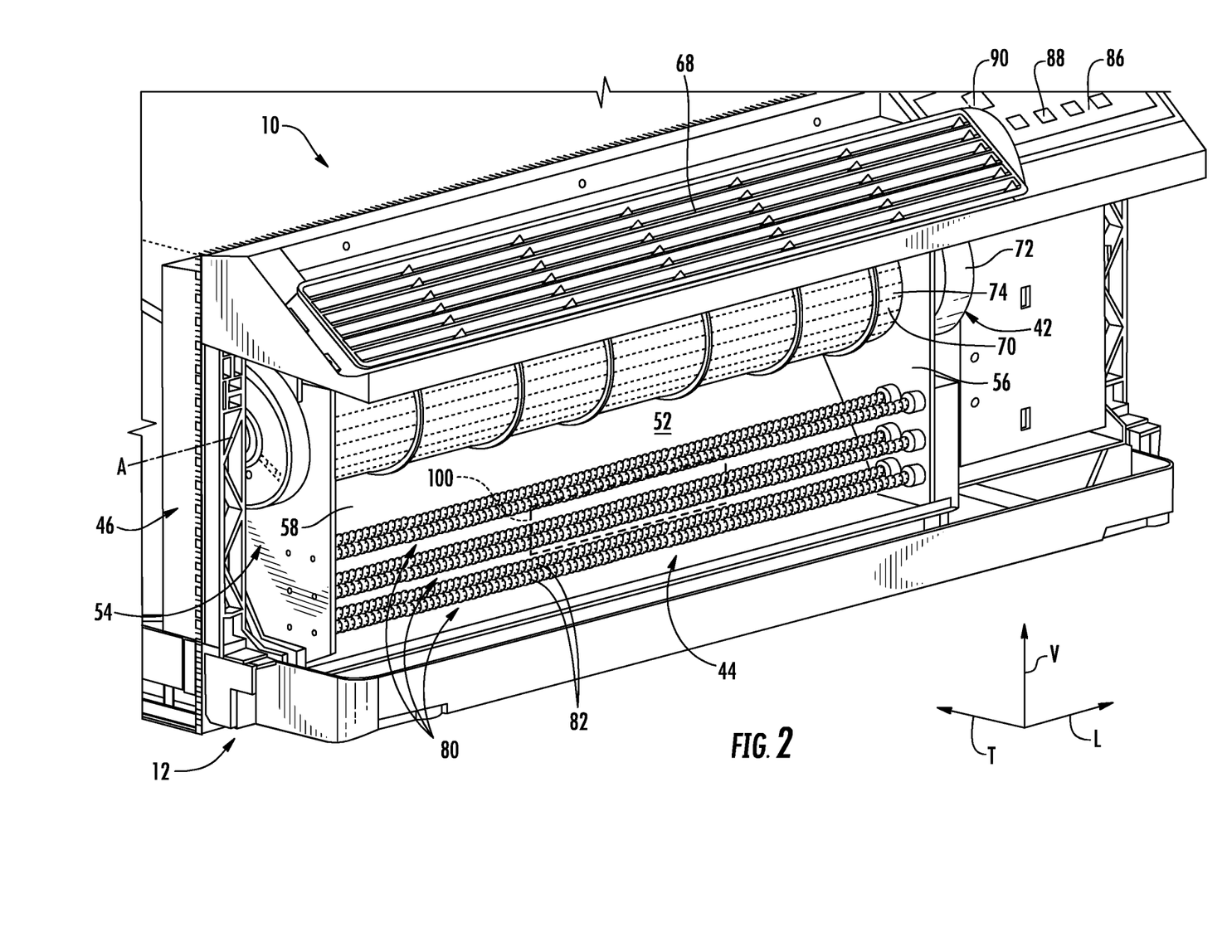
FIG. 2 provides a perspective view of components of an indoor portion of the exemplary air conditioner unit of FIG. 1.

Referring now also to FIG. 2, indoor portion 12 may include, for example, an indoor heat exchanger 40, an indoor or blower fan 42, and a heating unit 44. These components may, for example, be housed behind the room front 24 of housing 20. Additionally, a bulkhead 46 of housing 20 may generally support or house various other components or portions thereof of the indoor portion 12, such as the blower fan 42 and the heating unit 44. Bulkhead 46 may generally separate and define the indoor portion 12 and outdoor portion 14.

Figure 3:
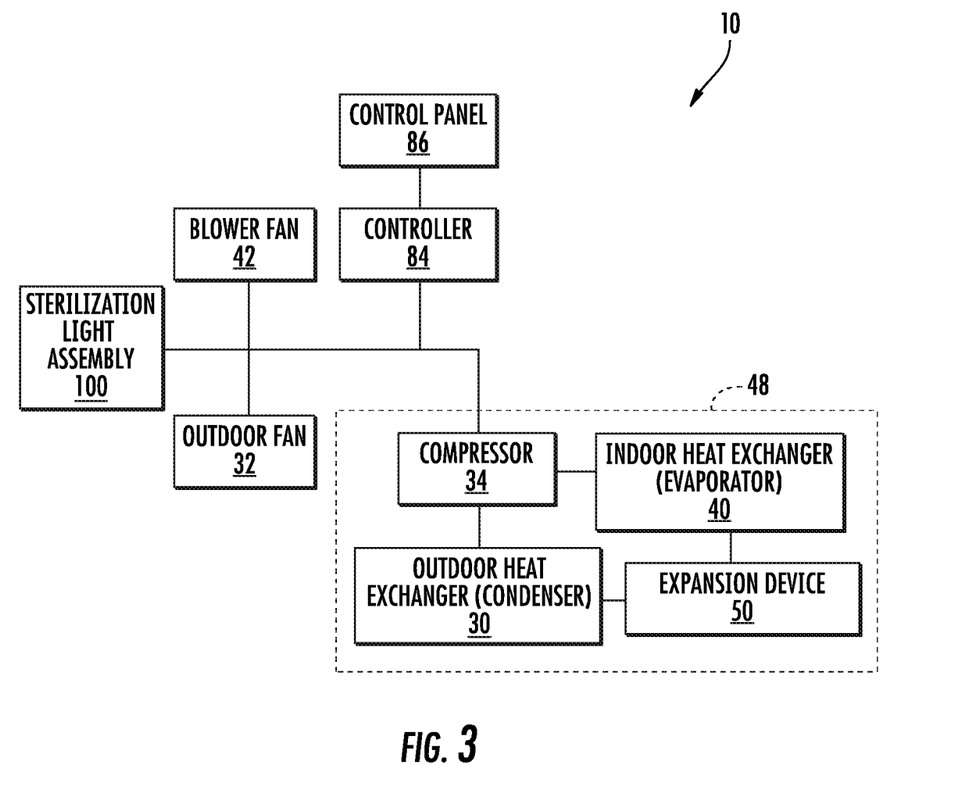
FIG. 3 provides a schematic view of a refrigeration loop in accordance with exemplary embodiments of the present disclosure.

Outdoor and indoor heat exchangers 30, 40 may be components of a refrigeration loop 48, which is shown schematically in FIG. 3. Refrigeration loop 48 may, for example, further include compressor 34 and an expansion device 50. As illustrated, compressor 34 and expansion device 50 may be in fluid communication with outdoor heat exchanger 30 and indoor heat exchanger 40 to flow refrigerant therethrough as is generally understood. More particularly, refrigeration loop 48 may include various lines for flowing refrigerant between the various components of refrigeration loop 48, thus providing the fluid communication there between. Refrigerant may thus flow through such lines from indoor heat exchanger 40 to compressor 34, from compressor 34 to outdoor heat exchanger 30, from outdoor heat exchanger 30 to expansion device 50, and from expansion device 50 to indoor heat exchanger 40. The refrigerant may generally undergo phase changes associated with a refrigeration cycle as it flows to and through these various components, as is generally understood. One suitable refrigerant for use in refrigeration loop 48 is 1,1,1,2-Tetrafluoroethane, also known as R-134A, although it should be understood that the present disclosure is not limited to such example and rather that any suitable refrigerant may be used.

As is understood, refrigeration loop 48 may be alternately operated as a refrigeration assembly (and thus perform a refrigeration cycle) or a heat pump (and thus perform a heat pump cycle). When refrigeration loop 48 is operating in a cooling mode and thus performs a refrigeration cycle, the indoor heat exchanger 40 acts as an evaporator and the outdoor heat exchanger 30 acts as a condenser. Alternatively, when the assembly is operating in a heating mode and thus performs a heat pump cycle, the indoor heat exchanger 40 acts as a condenser and the outdoor heat exchanger 30 acts as an evaporator. The outdoor and indoor heat exchangers 30, 40 may each include coils through which a refrigerant may flow for heat exchange purposes, as is generally understood.

In exemplary embodiments, expansion device 50 is disposed in the outdoor portion 14 between the indoor heat exchanger 40 and the outdoor heat exchanger 30. Optionally, expansion device 50 may be an electronic expansion valve that enables controlled expansion of refrigerant, as is generally understood. More specifically, electronic expansion device 50 may be configured to precisely control the expansion of the refrigerant to maintain, for example, a desired temperature differential of the refrigerant across the indoor heat exchanger 40. In other words, electronic expansion device 50 throttles the flow of refrigerant based on the reaction of the temperature differential across indoor heat exchanger 40 or the amount of superheat temperature differential, thereby ensuring that the refrigerant is in the gaseous state entering compressor 34. In alternative embodiments, expansion device 50 may be a capillary tube or another suitable expansion device configured for use in a thermodynamic cycle.

Figure 4:
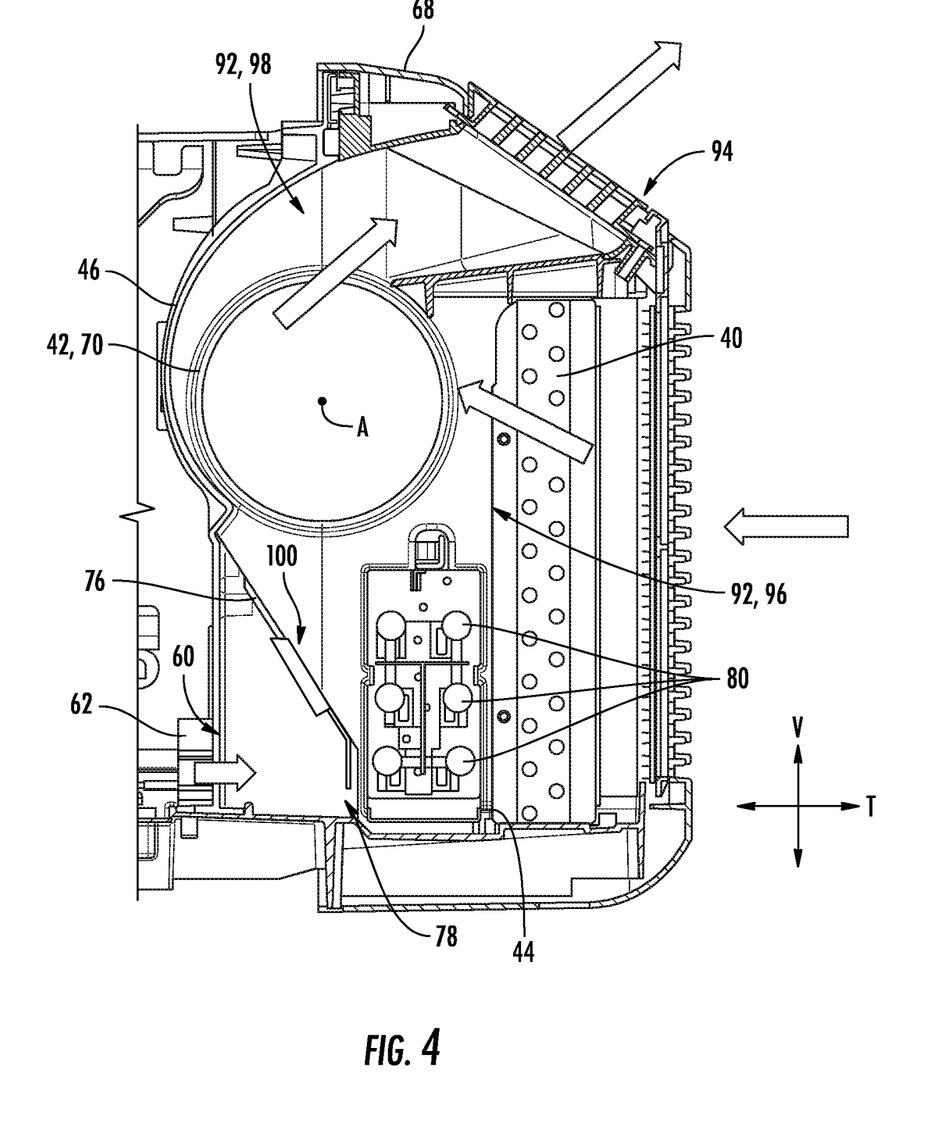
FIG. 4 provides a side sectional view of components of an indoor portion of the exemplary air conditioner unit of FIG. 1.

Turning generally to FIGS. 1, 2, and 4, bulkhead 46 may include various peripheral surfaces that define an interior 52 thereof. For example, bulkhead 46 may include a first sidewall 54 and a second sidewall 56 which are spaced apart from each other along the lateral direction L. A rear wall 58 may extend laterally between the first sidewall 54 and second sidewall 56. The rear wall 58 may, for example, include an upper portion and a lower portion. The lower portion may have a generally linear cross-sectional shape, and may be positioned below the upper portion along the vertical direction V. Rear wall 58 may further include an indoor facing surface and an opposing outdoor facing surface. The indoor facing surface may face the interior 52 and indoor portion 12, and the outdoor facing surface may face the outdoor portion 14. As will be described in greater detail below, a sterilization light assembly 100 may be mounted proximal to bulkhead 46 or otherwise within indoor portion 12 (e.g., on a heat shield 76) to sterilize or otherwise reduce microbes, bacteria, or viruses within air in indoor portion 12.

As shown, a head unit 68 may be attached to or included with housing 20 (e.g., on or adjacent to bulkhead 46, such as on the upper portion). Specifically, the head unit 68 may be positioned at or above the indoor portion 12 as part of the housing 20. In some such embodiments, the head unit 68 is further positioned above the blower fan 42. In additional or alternative embodiments, the head unit 68 extends at least from the first sidewall 54 to the second sidewall 56. Generally, the head unit 68 may define an exhaust outlet 94 having one or more openings through which air may flow (e.g., from the indoor portion 12 to the corresponding room). In some embodiments, head unit 68 further includes a cutoff panel 110 (e.g., extending below the exhaust outlet 94) to cutoff or separate portions of an airflow path 92 upstream from the blower fan 42 and downstream from the blower fan 42. Specifically, cutoff panel 110 may help direct air along an airflow path 92 of the indoor portion 12 and across the blower fan 42 before such being expelled through the exhaust outlet 94.

In some embodiments, the upper portion of the bulkhead 46 has a generally curvilinear cross-sectional shape, and may accommodate a portion of the blower fan 42, which may be, for example, a tangential fan. Blower fan 42 may include a blade assembly 70 and a motor 72. The blade assembly 70 may include one or more metal blades (i.e., formed from a suitable metal, such as aluminum or steel, including alloys thereof) disposed about a hollow core. When assembled, the blade disposed within a fan housing 74, may be disposed at least partially within the interior 52 of the bulkhead 46, such as within the upper portion. As shown, blade assembly 70 may for example extend along the lateral direction L between the first sidewall 54 and the second sidewall 56. The motor 72 may be connected to the blade assembly 70, such as through the housing 74 to the blades via a shaft extending along a rotation axis. Operation of the motor 72 may rotate the blades or blade assembly 70 about the rotation axis, thus generally operating the blower fan 42 to motivate air through the indoor portion 12. Further, in exemplary embodiments, motor 72 may be disposed exterior to the bulkhead 46. Accordingly, the shaft may for example extend through one of the sidewalls 54, 56 to connect the motor 72 and blade assembly 70.

According to the illustrated embodiment, blower fan 42 may operate as an evaporator fan in refrigeration loop 48 to encourage the flow of air through indoor heat exchanger 40. Accordingly, blower fan 42 may be positioned downstream of indoor heat exchanger 40 along the flow direction of indoor air and downstream of heating unit 44 along the flow direction of outdoor air (e.g., when make-up air is being supplied to indoor portion 12). In some such embodiments, blower fan 42 is disposed between a separate intake segment 96 and exhaust segment 98 of the airflow path 92 for indoor air through indoor portion 12. As shown, the intake segment 96 may extend from the intake openings of the room front 24 to the blower fan 42 such that the indoor heat exchanger 40 is disposed along or within the intake segment 96. The exhaust segment 98 may extend from the blower fan 42 to the exhaust outlet 94. Thus, blower fan 42 may be downstream from the intake segment 96 of the indoor portion 12 while being upstream from the exhaust outlet 94 and exhaust segment 98 of the indoor portion 12. Moreover, the cutoff panel 110 may separate or otherwise be disposed between the intake segment 96 and the exhaust segment 98.

Heating unit 44 in exemplary embodiments includes one or more heater banks 80 (e.g., disposed within the intake segment 96). Each heater bank 80 may be operated as desired to produce heat. In some embodiments, as shown, three heater banks 80 may be used. Alternatively, however, any suitable number of heater banks 80 may be used. Each heater bank 80 may further include at least one heater coil or coil pass 82, such as in exemplary embodiments two heater coils or coil passes 82. Alternatively, other suitable heating elements may be used.

In some embodiments, a heat shield 76 is mounted within indoor portion 12 to absorb, block, or reflect heat, such as the heat generated at heating unit 44. For instance, heat shield 76 may be mounted proximal to heating unit 44 or within intake segment 96. In particular, heat shield 76 may be disposed between heating unit 44 and at least a portion of bulkhead 46 (e.g., along the transverse direction T). In certain embodiments, heat shield 76 extends forward from an upper end 76A to a lower end 76B. Upper end 76A may be disposed on or proximal to bulkhead 46 (e.g., below blower fan 42) while lower end 76B is disposed adjacent or proximal to heating unit 44. Thus, heat shield 76 may define an angle that is nonparallel or nonorthogonal to the vertical direction V or the transverse direction T. Optionally, the lower end 76B or at least a portion thereof may be held or spaced apart from a lower wall or basepan within indoor portion 12. Thus, a gap or opening 78 may be defined (e.g., along the transverse direction T) below heat shield 76 permitting air to flow forward from a back side to a front side of heat shield 76. As shown, the gap or opening 78 may be defined at a lower height than one or more heater banks 80. Additionally or alternatively, the gap or opening 78 may be in lateral or vertical alignment with a vent aperture 60 (e.g., while being spaced apart from the vent aperture 60 along the transverse direction T).

Generally, heat shield 76 may be formed from an suitable material to prevent or restrict the transmission of heat from one portion or side of indoor portion 12 to another portion or side of housing 20 (e.g., aluminum or steel, including alloys thereof).

The operation of air conditioner unit 10 including compressor 34 (and thus refrigeration loop 48 generally), blower fan 42, outdoor fan 32, heating unit 44, expansion device 50, and other components of refrigeration loop 48 may be controlled by a processing device such as a controller 84. Controller 84 may be in communication (via for example a suitable wired or wireless connection) to such components of the air conditioner unit 10. By way of example, the controller 84 may include a memory and one or more processing devices such as microprocessors, CPUs or the like, such as general or special purpose microprocessors operable to execute programming instructions or microcontrol code associated with operation of unit 10. The memory may represent random access memory such as DRAM, or read only memory such as ROM or FLASH. In one embodiment, the processor executes programming instructions stored in memory. The memory may be a separate component from the processor or may be included onboard within the processor.

Unit 10 may additionally include a control panel 86 and one or more user inputs 88, which may be included in control panel 86. The user inputs 88 may be in communication with the controller 84. A user of the unit 10 may interact with the user inputs 88 to operate the unit 10, and user commands may be transmitted between the user inputs 88 and controller 84 to facilitate operation of the unit 10 based on such user commands. A display 90 may additionally be provided in the control panel 86, and may be in communication with the controller 84. Display 90 may, for example be a touchscreen or other text-readable display screen, or alternatively may simply be a light that can be activated and deactivated as required to provide an indication of, for example, an event or setting for the unit 10.

Figure 8:
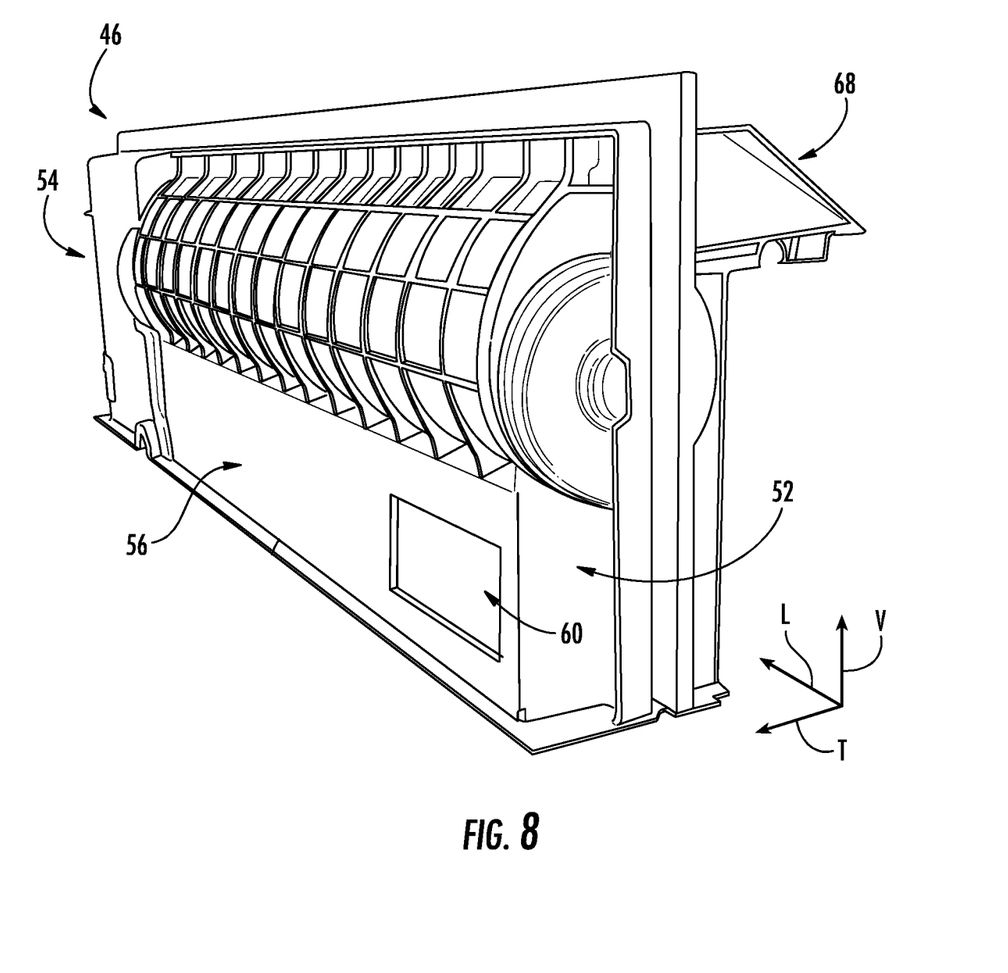
FIG. 8 provides a rear perspective view of a bulkhead assembly in accordance with exemplary embodiments of the present disclosure.

Referring briefly to FIGS. 4 and 8, a vent aperture 60 may be defined in the rear wall 58 of bulkhead 46. Vent aperture 60 may allow air flow therethrough between the indoor portion 12 and outdoor portion 14, and may be utilized in an installed air conditioner unit 10 to allow outdoor air to flow therethrough into the room through the indoor portion 12. In this regard, in some cases it may be desirable to allow outside air to flow into the room in order to compensate for negative pressure created within the room (e.g., by turning on a bathroom fan). In this manner, according to an exemplary embodiment, outside air, also referred to as make-up air, may be provided into the room through vent aperture 60 when a negative pressure is created as air is drawn out of the room by, for example, a bathroom fan.

Optionally, blower fan 42 and outdoor fan 32 may be used (e.g., selectively activated) to provide make-up air into the room when desired. Additionally or alternatively, air conditioner unit 10 may further include an auxiliary fan 62 that may be used with the existing refrigeration loop 48 to force additional outdoor air through vent aperture 60. Auxiliary fan 62 may, according to the illustrated example embodiment, be positioned within outdoor portion 14 proximate to vent aperture 60. Additionally or alternatively, auxiliary fan 62 may be partially or wholly disposed in vent aperture 60 or partially or wholly disposed in indoor portion 12. Accordingly, auxiliary fan 62 may induce a flow of outdoor air from the outdoor or ambient environment through vent aperture 60 to the indoor portion 12.

Separate from or in addition to auxiliary fan 62, a damper may be pivotally mounted to the bulkhead 46 proximate to vent aperture 60 to open and close vent aperture 60. For instance, a damper may be pivotally mounted to the indoor facing surface of indoor portion 12. The damper may be configured to pivot between a first, closed position where damper prevents air from flowing between outdoor portion 14 and indoor portion 12, and a second, open position where damper is spaced apart from vent aperture 60 (e.g., positioned parallel to heat shield 76) and allows make-up air to flow into the room. Optionally, the damper may be pivoted between the open and closed position by an electric motor in mechanical communication with damper and controlled by controller 84, or by any other suitable method (e.g., passively in response to pressure generated by fan 62 or 42).

Referring more broadly to FIGS. 4 through 7, greater detail of unit 10 is provided, in particular regarding sterilization light assembly 100. Generally, sterilization light assembly 100 is held or disposed within the indoor portion 12 (e.g., at the intake segment 96) to transmit an ultraviolet light emission to air residing or flowing through indoor portion 12 (e.g., from vent aperture 60). To this end, sterilization light assembly 100 includes one or more ultraviolet (UV) light sources 102 (e.g., light emitting diodes or LEDs) configured to emit radiation in the germicidal wavelength range of 100 to 300 nanometers. Optionally, one or more light sources 102 may be ultraviolet C (UVC) light sources 102 configured to emit radiation between 200 to 280 nanometers or 245 to 265 nanometers.

In some embodiments, sterilization light assembly 100 is directed rearward (e.g., at or in the general direction of bulkhead 46). For instance, sterilization light assembly 100 may be directed, at least in part, toward vent aperture 60. For instance, sterilization light assembly may be directed generally downward and rearward (e.g., at a nonparallel and nonorthogonal angle relative to the vertical direction V and the transverse direction T). In turn, light emissions from sterilization light assembly 100 may generally be projected or guided upstream to a region apart from intake segment 96, such as to the vent aperture 60 or make-up air flowing therefrom. At least a portion of the UV light emissions from sterilization light assembly 100 may be projected or guided toward vent aperture 60, or otherwise to a flow path directing make-up air to airflow path 92. During use, bulkhead 46 and heat shield 76 may generally block or prevent UV light emissions from escaping housing 20. For instance, sterilization light assembly 100 may be held above (e.g., at a greater vertical height than) vent aperture 60. Moreover, bulkhead 46 may span the projected field or area of sterilization light assembly 100. Reflected light emissions may be blocked, for instance, by heat shield 76 or the other surrounding portions of housing 20. Advantageously, transmission of UV light from housing 20 may be limited while ensuring transmission of UV light to the make-up air.

As shown, sterilization light assembly 100 may further be disposed upstream from blower fan 42 and at least a portion of the intake segment 96. For instance, sterilization light assembly 100 may be disposed at a point in the flow path for make-up air that is downstream from indoor heat exchanger 40 while being upstream from blower fan 42. During use, make-up air drawn to blower fan 42 may thus be subjected to UV light emissions or radiation, thereby advantageously reducing or eliminating active microbes, bacteria, or viruses within the air before they reach the exhaust segment 98.

As noted above, head unit 68 may define air exhaust outlet 94. Specifically, air exhaust outlet 94 may be defined above at least a portion of blower fan 42 along the vertical direction V or forward from blower fan 42 along the transverse direction T. Cutoff panel 110 may, thus, extend along the transverse direction T while separating or being disposed between the intake segment 96 and the exhaust segment 98 along the vertical direction V. In some such embodiments, sterilization light assembly 100 is disposed below exhaust outlet 94 along the vertical direction V (e.g., at a lower relative height than exhaust outlet 94). For instance, sterilization light assembly 100 may be attached to the heat shield 76, such as by a mounting bracket 104 that holds sterilization light assembly 100 and is joined to heat shield 76 (e.g., via a suitable mechanical fastener, adhesive, etc.).

Figure 5:
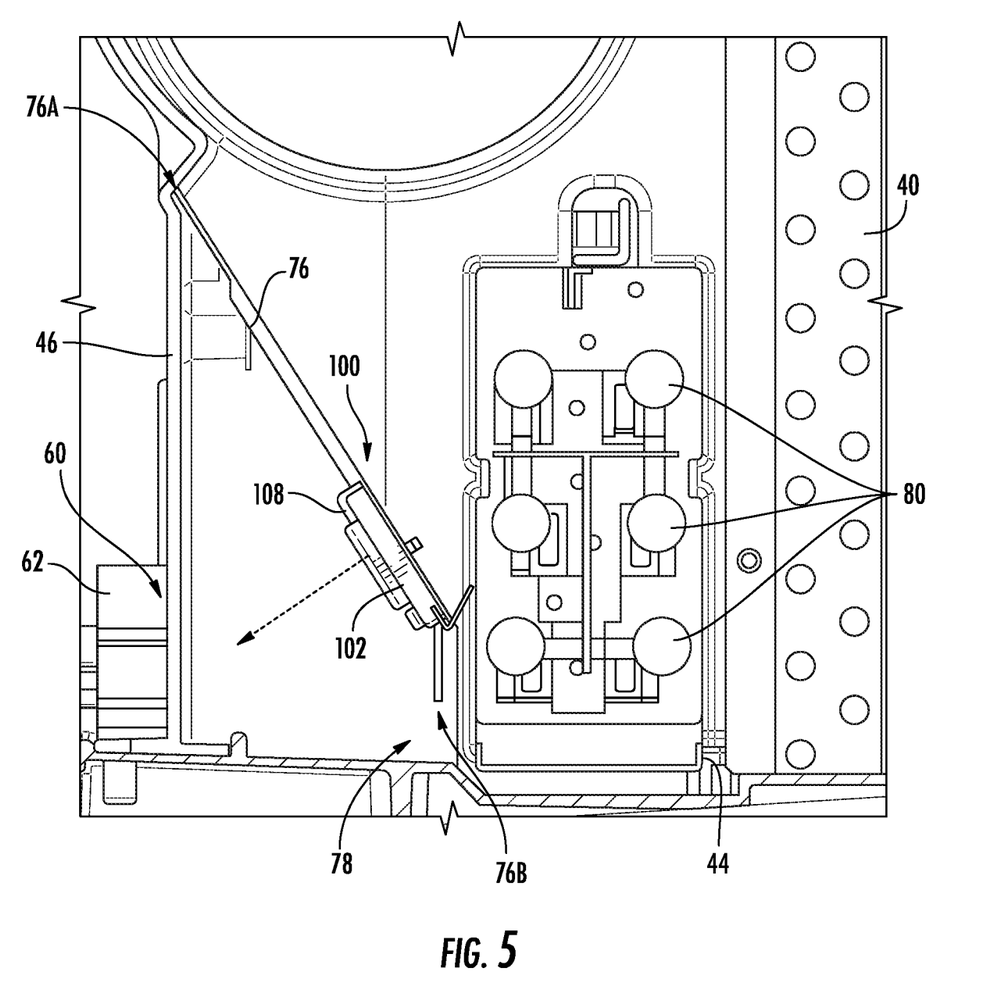
FIG. 5 provides a magnified side sectional view of components of the indoor portion of the exemplary air conditioner unit of FIG. 1.
Figure 6:
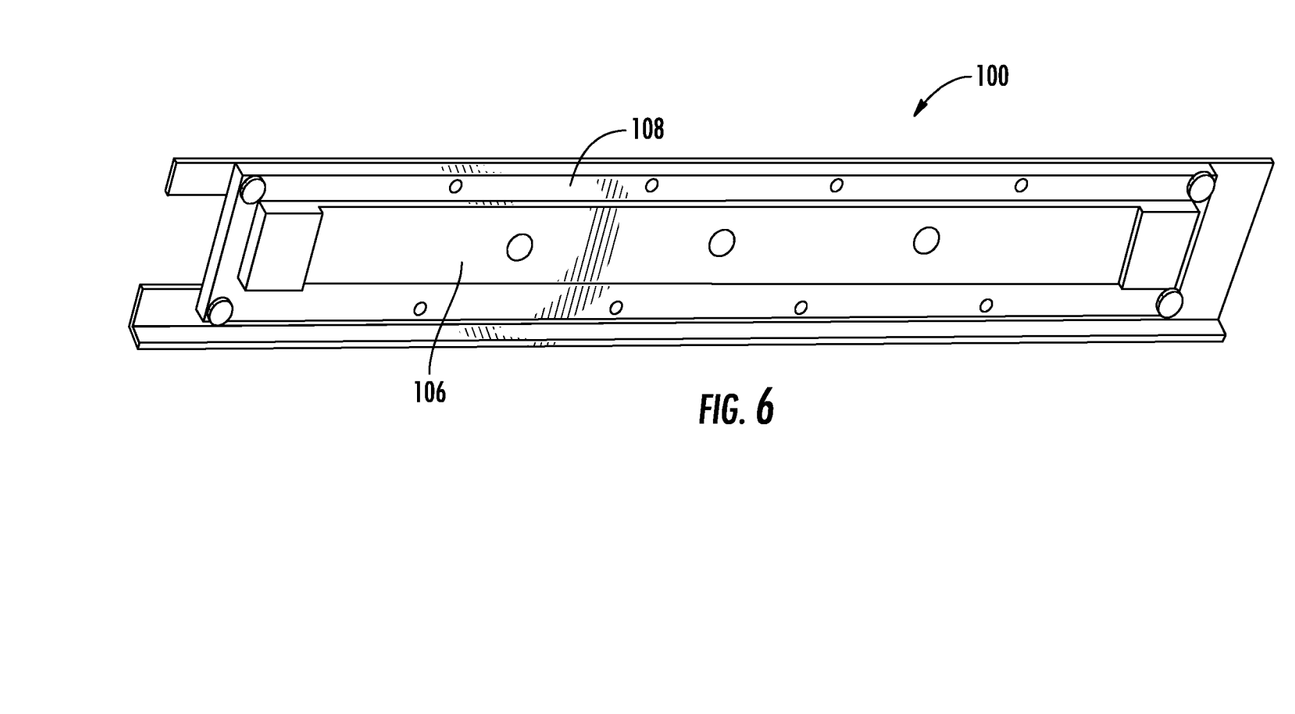
FIG. 6 provides a bottom perspective view of a cutoff panel and sterilization light assembly, in isolation, of the exemplary air conditioner unit of FIG. 1.

In the illustrated embodiments, sterilization light assembly 100 is disposed below blower fan 42. Specifically, sterilization light assembly 100 may be mounted directly beneath blower fan 42. Optionally, sterilization light assembly 100 may be held rearward from a front end of blower fan 42 (i.e., rearward from the frontmost portion of blower fan 42, such as might be disposed within intake segment 96). Moreover, heat shield 76 (and thus sterilization light assembly 100) may also be disposed below (i.e., at a lower height) than a bottom end of blower fan 42.

As described, sterilization light assembly 100 may be disposed upstream from blower fan 42. For instance, sterilization light assembly 100 may be disposed along the airflow path 92 between heating unit 44 and blower fan 42. Additionally or alternatively, the mounting bracket 104 supporting the sterilization light assembly 100 within the indoor portion 12 may be formed from or include a metal material (e.g., aluminum or steel, including alloys thereof). When assembled, mounting bracket 104 may have a back face opposite of the sterilization light assembly 100 and generally facing the upstream portion of intake segment 96. Thus, air drawn along the intake segment 96 may contact the back face of mounting bracket 104. Notably, air drawn along the airflow path 92 to blower fan 42 may aid in cooling sterilization light assembly 100. For instance, heat may be conducted through mounting bracket 104 and to the air flowing through intake segment 96. Optionally, controller 84 may be configured to restrict activation of sterilization light assembly 100 (e.g., to project UV emissions therefrom) unless blower fan 42 is activated (e.g., rotated to draw air along intake segment 96). Thus, activation of sterilization light assembly 100 may be contingent on blower fan 42 being activated to draw air thereto.

Figure 7:
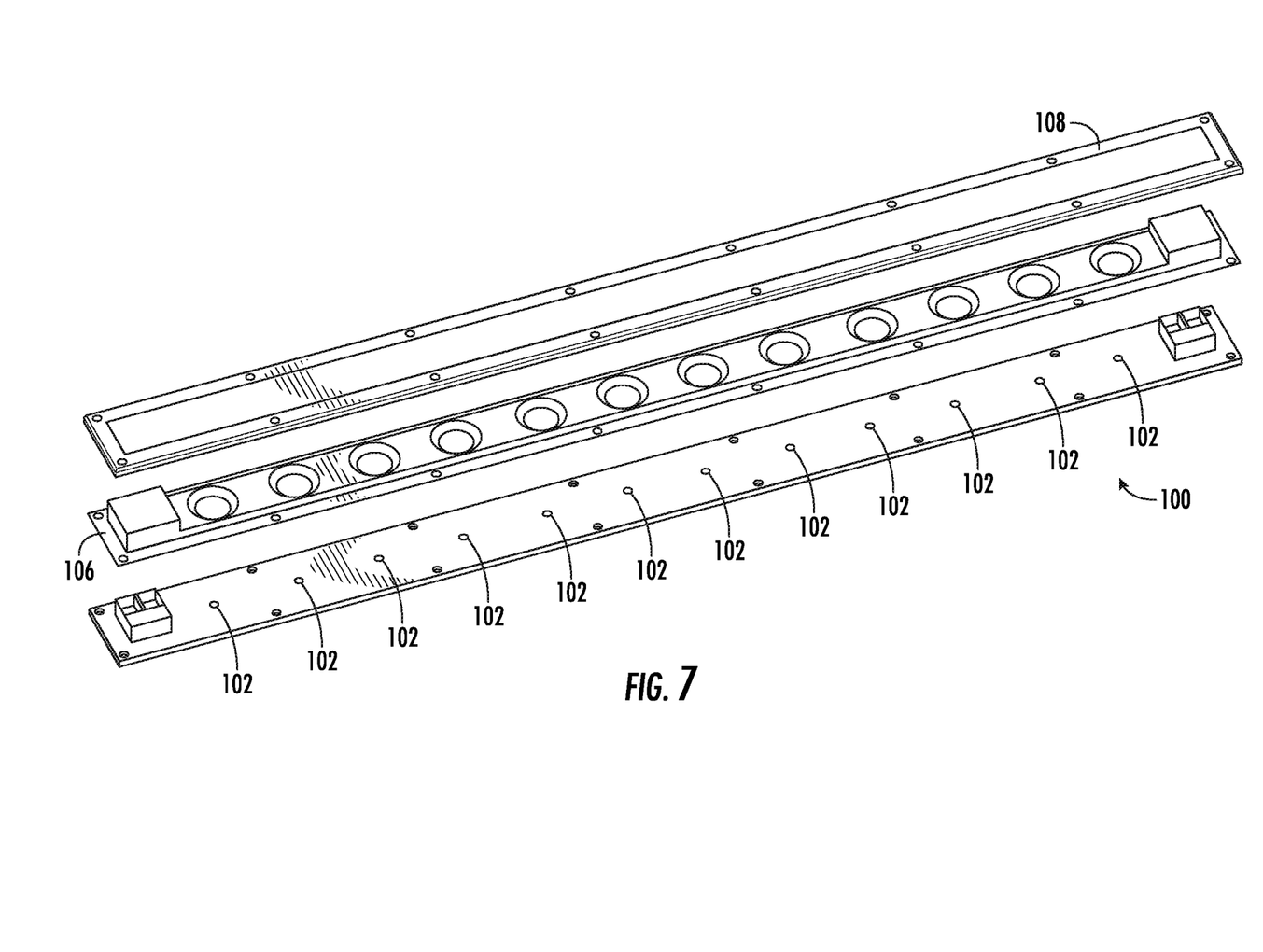
FIG. 7 provides an exploded perspective view of an exemplary sterilization light assembly of an air conditioner unit according to exemplary embodiments of the present disclosure.

In certain embodiments, one or more UV light sources 102 of sterilization light assembly 100 are advantageously covered or sealed (e.g., to prevent the passage of moisture thereto, which might otherwise be significant or problematic within make-up air, such as in humid climates). For instance, a lens casing 106 (e.g., UV-transparent lens casing) may seal at least one light source 102 (e.g., and a control board thereof) against mounting bracket 104. Optionally, a peripheral bracket 108 may extend about a rim of the lens casing 106 to sandwich the rim against mounting bracket 104 and, thus, hold lens casing 106 to mounting bracket 104. Although most solid materials absorb significant portions of UV light, lens casing 106 may be formed from a UV-permissive polymer (e.g., configured to absorb less than 60% of UV emissions from sterilization light assembly 100).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An air conditioner unit for conditioning an indoor space, the air conditioner unit comprising:
    a housing defining an indoor portion and an outdoor portion, the housing further defining an exhaust outlet downstream from the indoor portion to exhaust air therefrom;
    an outdoor heat exchanger assembly disposed in the outdoor portion and comprising an outdoor heat exchanger;
    an indoor heat exchanger assembly disposed in the indoor portion and comprising an indoor heat exchanger and an indoor fan;
    a compressor in fluid communication with the outdoor heat exchanger and the indoor heat exchanger to circulate a refrigerant between the outdoor heat exchanger and the indoor heat exchanger; and
    a bulkhead disposed between the outdoor heat exchanger and the indoor heat exchanger along a transverse direction, the bulkhead defining the indoor portion and the outdoor portion, the bulkhead may define a vent aperture therethrough; and
    a sterilization light assembly disposed within the indoor portion downstream from the vent aperture,
    wherein the sterilization light assembly is directed rearward away from the indoor heat exchanger.

2. The air conditioner unit of claim 1, wherein the sterilization light assembly is disposed downstream from the indoor heat exchanger.

3. The air conditioner unit of claim 1, wherein the indoor fan is disposed upstream of the sterilization light assembly.

4. The air conditioner unit of claim 1, wherein the sterilization light assembly is directed toward the vent aperture.

5. The air conditioner unit of claim 1, further comprising:
    a heat shield disposed within the indoor portion between the bulkhead and the indoor heat exchanger,
    wherein the sterilization light assembly is mounted on the heat shield.

6. The air conditioner unit of claim 1, wherein the sterilization light assembly is spaced apart from the bulkhead along a transverse direction.

7. The air conditioner unit of claim 1, wherein the indoor fan is disposed along an airflow path between an intake segment of the indoor portion and an exhaust segment of the indoor portion upstream from the exhaust outlet, wherein the air conditioner unit further comprises a cutoff panel separating the intake segment from the exhaust segment, and wherein the sterilization light assembly is mounted below the cutoff panel.

8. The air conditioner unit of claim 1, further comprising a metal mounting bracket supporting the sterilization light assembly within the indoor portion.

9. The air conditioner unit of claim 8, wherein the sterilization light assembly comprises
    an ultraviolet C (UVC) light source configured to emit radiation between 200 to 280 nanometers, and
    a lens casing sealing the UVC light source against the metal mounting bracket to prevent moisture from contacting the UVC light source.

10. An air conditioner unit for conditioning an indoor space, the air conditioner unit comprising:
    a housing defining an indoor portion and an outdoor portion, the housing further defining an exhaust outlet downstream from the indoor portion to exhaust air therefrom;
    an outdoor heat exchanger assembly disposed in the outdoor portion and comprising an outdoor heat exchanger;
    an indoor heat exchanger assembly disposed in the indoor portion and comprising an indoor heat exchanger and an indoor fan;
    a compressor in fluid communication with the outdoor heat exchanger and the indoor heat exchanger to circulate a refrigerant between the outdoor heat exchanger and the indoor heat exchanger; and
    a bulkhead disposed between the outdoor heat exchanger and the indoor heat exchanger along a transverse direction, the bulkhead defining the indoor portion and the outdoor portion, the bulkhead may define a vent aperture therethrough; and a sterilization light assembly disposed within the indoor portion downstream from the vent aperture and below the indoor fan, the sterilization light assembly being directed at the vent aperture to sterilize makeup air therefrom, wherein the sterilization light assembly is directed rearward away from the indoor heat exchanger.

11. The air conditioner unit of claim 10, wherein the sterilization light assembly is disposed downstream from the indoor heat exchanger.

12. The air conditioner unit of claim 10, wherein the indoor fan is disposed upstream of the sterilization light assembly.

13. The air conditioner unit of claim 10, further comprising:
a heat shield disposed within the indoor portion between the bulkhead and the indoor heat exchanger,
wherein the sterilization light assembly is mounted on the heat shield.

14. The air conditioner unit of claim 10, wherein the sterilization light assembly is spaced apart from the bulkhead along a transverse direction.

15. The air conditioner unit of claim 10, wherein the indoor fan is disposed along an airflow path between an intake segment of the indoor portion and an exhaust segment of the indoor portion upstream from the exhaust outlet, wherein the air conditioner unit further comprises a cutoff panel separating the intake segment from the exhaust segment, and wherein the sterilization light assembly is mounted below the cutoff panel.

16. The air conditioner unit of claim 10, further comprising a metal mounting bracket supporting the sterilization light assembly within the indoor portion.

17. The air conditioner unit of claim 16, wherein the sterilization light assembly comprises
an ultraviolet C (UVC) light source configured to emit radiation between 200 to 280 nanometers, and
a lens casing sealing the UVC light source against the metal mounting bracket to prevent moisture from contacting the UVC light source.

18. An air conditioner unit for conditioning an indoor space, the air conditioner unit comprising:
a housing defining an indoor portion and an outdoor portion, the housing further defining an exhaust outlet downstream from the indoor portion to exhaust air therefrom;
an outdoor heat exchanger assembly disposed in the outdoor portion and comprising an outdoor heat exchanger;
an indoor heat exchanger assembly disposed in the indoor portion and comprising an indoor heat exchanger and an indoor fan;
a compressor in fluid communication with the outdoor heat exchanger and the indoor heat exchanger to circulate a refrigerant between the outdoor heat exchanger and the indoor heat exchanger;
a bulkhead disposed between the outdoor heat exchanger and the indoor heat exchanger along a transverse direction, the bulkhead defining the indoor portion and the outdoor portion, the bulkhead may define a vent aperture therethrough;
a heat shield disposed within the indoor portion between the bulkhead and the indoor heat exchanger; and
a sterilization light assembly mounted on the heat shield within the indoor portion downstream from the vent aperture.

19. The air conditioner unit of claim 18, wherein the sterilization light assembly is directed toward the vent aperture downstream from the indoor heat exchanger.

20. The air conditioner unit of claim 18, wherein the indoor fan is disposed along an airflow path between an intake segment of the indoor portion and an exhaust segment of the indoor portion upstream from the exhaust outlet, wherein the air conditioner unit further comprises a cutoff panel separating the intake segment from the exhaust segment, and wherein the sterilization light assembly is mounted below the cutoff panel.

* * * * *